Figure 1:
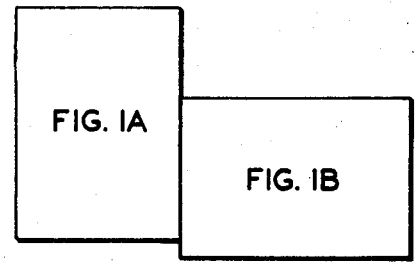

United States Patent [19]

Saporito et al.

[11] Patent Number: 4,663,727

[45] Date of Patent: May 5, 1987

[54] ULTRASONIC INSPECTION SYSTEM

[75] Inventors: Michael J. Saporito; Salvatore J. Deleo, both of Rochester; Paul A. Lewis, E. Bethany; Albert E. Curtis, III, Webster; Joseph D'Arienzo, Rochester, all of N.Y.; David P. Roller, Jr., Southhampton, Pa.

[73] Assignee: Rochester Gas & Electric Corp., Rochester, N.Y.

[21] Appl. No.: 601,883

[22] Filed: Apr. 19, 1984

[51] Int. Cl.$^4$ .................. G01N 29/04; G06F 15/46
[52] U.S. Cl. .................................. 364/551; 73/623; 73/638; 364/552
[58] Field of Search .................. 364/551, 552; 73/621–623, 637, 638

[56] References Cited

U.S. PATENT DOCUMENTS

| | | | |
|---|---|---|---|
| 3,583,211 | 6/1971 | Brech | 73/623 |
| 3,766,775 | 10/1973 | Gunkel | 73/623 |
| 4,102,206 | 7/1978 | Perdijon | 73/623 X |
| 4,212,207 | 7/1980 | Conradi | 73/623 |
| 4,353,257 | 10/1982 | Vrba et al. | 73/623 |
| 4,453,410 | 6/1984 | Schmitz et al. | 73/623 X |
| 4,475,394 | 10/1984 | Takeda et al. | 73/621 |
| 4,520,671 | 6/1985 | Hardin | 73/621 X |
| 4,523,468 | 6/1985 | Derkacs et al. | 73/622 X |

Primary Examiner—Felix D. Gruber
Assistant Examiner—H. R. Herndon
Attorney, Agent, or Firm—Martin LuKacher

[57] ABSTRACT

An ultrasonic inspection system for inspecting areas of tubular members and providing a display of any internal flaws therein. In order to operate in a confined work space a probe containing ultrasonic transducers is provided together with a rotational and axial drive scanner which is linked to a remotely controlled manipulator. The scanner uses a wand supporting the probe at the upper end thereof. The manipulator locates the probe and scanner in alignment with the tube to be inspected. A stepping motor on the scanner drives the wand and the probe axially to a location just above the area to be inspected. A second stepping motor rotates the wand to enable the probe to perform a circumferential scan. The axial stepping motor then indexes the wand towards the lower edge of the area and another circumferential scan occurs. The indexing and circumferential scanning proceeds until the entire area is scanned. The signals received from the ultrasonic transducers are digitized and processed, with the aid of programmed digital computer, so as to graphically display the interior interface of the sleeve and tube which is scanned to show any voids as may be due to incomplete bonding between the sleeve and the tube.

19 Claims, 5 Drawing Figures

ULTRASONIC INSPECTION SYSTEM

DESCRIPTION

The present invention relates to ultrasonic inspection systems and particularly systems for the ultrasonic inspection of tubular members and the display of internal flaws in areas thereof under inspection.

The present invention is especially suitable for use in the ultrasonic inspection of tubes in steam generators, especially tubes which have been repaired by insertion of sleeves therein which are bonded to the original tubes in the areas in which the tubes are bonded together. The invention is generally useful for ultrasonic inspection of tubular members and for providing for displays of internal flaws in areas thereof such as may contain bonded joints to verify the integrity of such joints.

Ultrasonic testing has heretofore been used for nondestructive inspection and has found extensive medical applications. In order to perform ultrasonic testing of confined areas, such as in the tubes of steam generators where the work space is limited and where the testing must be remotely controlled, for example due to environmental considerations in the steam generators in nuclear plants, significant problems are presented. These problems are exacerbated by the requirement for high resolution testing which would reveal any flaws, such as voids, serious enough to constitute a leak path.

In accordance with the invention, an ultrasonic inspection system has been provided which delivers the ultrasonic energy to the area to be inspected, even though the area is well within the confines of a tubular member. Means are provided to couple the energy between an ultrasonic transducer and the surface of the tube without losses and spurious reflections. Means are also provided for scanning beams of ultrasonic energy over the area to be inspected and detecting reflections which represent the flaws (e.g. voids) in the interior of the area. Means are provided for processing these signals to produce a graphics display of the interior of the area which highlights any such flaws and depicts any voids serious enough to constitute a leak path.

Accordingly, it is an object of the present invention to provide an improved system for ultrasonic inspection, particularly of tubular members.

It is another object of the present invention to provide an improved ultrasonic inspection system which is remotely operable.

It is a still further object of the present invention to provide an improved ultrasonic inspection system which is operable in a confined work space.

It is a still further object of the present invention to provide and improved ultrasonic inspection system in which ultrasonic energy is delivered to and derived from a confined area within a tubular member so as to produce a high resolution image which depicts the interior of the area and shows any flaws, such as voids, which may constitute a leak path.

Briefly described, a system for the inspection of tubular members in accordance with the invention makes use of means for transmitting ultrasonic signals in a direction from the interior towards the exterior of the member and receiving reflections from any discontinuity in the material of the member. Means are provided for scanning the signals circumferentially around and axially along the tubular member. Means are also provided for processing the received signals to produce a display of the internal cross section of the member defined by the area over which the signals are scanned which depicts any discontinuities therein.

Figure 2:
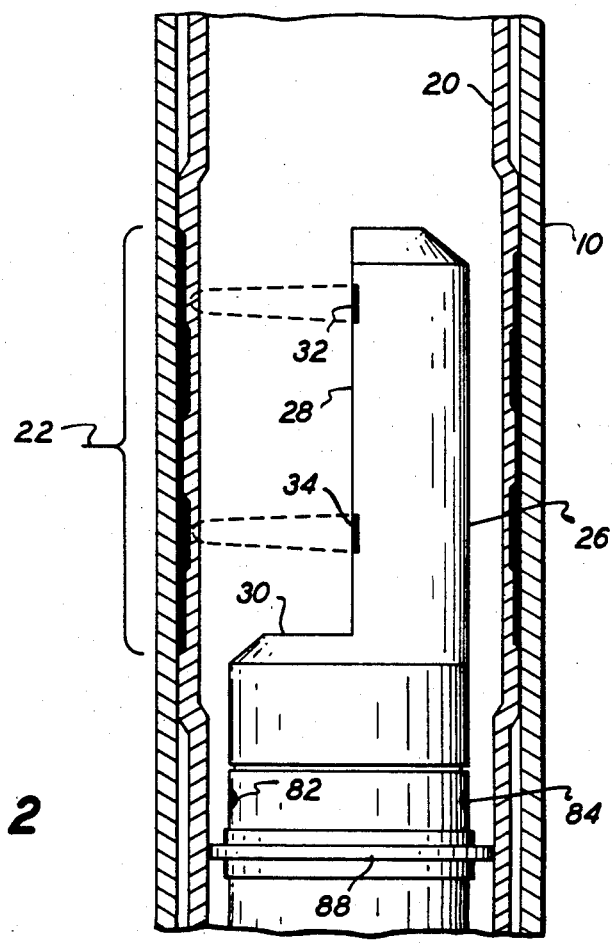
Figure 3:
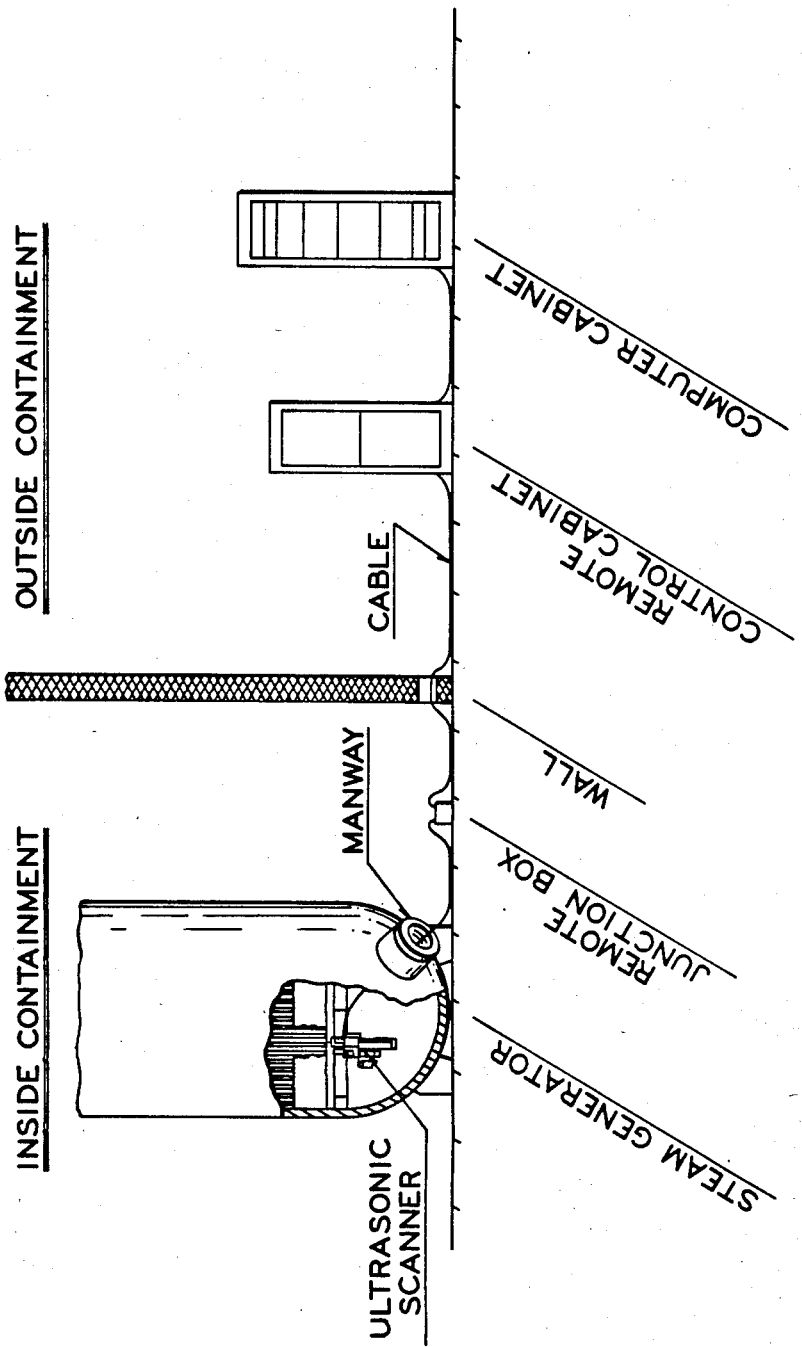

The foregoing and other objects, features and advantages of the present invention as well as a presently preferred embodiment thereof will be more apparent from a reading of the following description in connection with the accompanying drawings in which:

FIG. 1 (shown in two parts as FIGS. 1A and 1B) is a diagrammatic view of a system for ultrasonic inspection of tubes of a steam generator which have been repaired by insertion of sleeves, bonded to the original tubes in a region axially spaced from the lower end of the tubes, which system provides a graphics display of the interior of the region which reveals voids large enough to provide a leak path;

FIG. 2 is an enlarged view illustrating the region of the sleeved tube which is inspected and showing the probe and upper end of the wand which supports and provides part of the mechanism for scanning the region; and FIG. 3 is diagrammic view of the system installed for testing of the sleeved tubes of the steam generator of a nuclear power plant.

Referring more particularly to the drawings, there is shown three adjacent tubes, 10, 12 and 14 of the tubes in a steam generator. The steam generator contains 3,260 or more such tubes through which pressurized hot water is circulated. The tubes are retained between the tube sheet 16 and the first support plate 18. Water is circulated through the tubes above the lower sheet 16 and converts water on the outside diameter of the tubes into steam which drives the turbine. The turbine in turn drives the generators which produce electricity.

The lower sheet 16 may be approximately 22 inches long in a direction axially of the tubes. The tubes may be approximately 50 inches long between the tube sheet 16 and the tube support plate. The original tubes are illustrated by the tube 12. When an original tube deteriorates, it may be repaired by the insertion of a sleeve 20, as shown in the tube 10. Leak tight seals between the original tube and the sleeve are provided in areas or regions 22 between the sheets 16 and 18 as well as in regions 24 adjacent to the lower ends of the tube and sleeve in the tube sheet 16. The original tubes 10, 12 and 14 are suitably made of a nickel alloy (Inconel). The sleeve 20 is also made of the same nickel alloy (Inconel) having an outer layer of metallurgically bonded nickel. The sleeve is also provided with a pair of machined grooves filled with a gold braze alloy in the area to be bonded. In providing the bond, the sleeve is explosively expanded in the region 22 and then heated so as to provide a seal by means of the gold braze in the region 22. After the seal is made in the region 22, an explosive charge is detonated at the lower end of the sleeve to metallurgically bond the sleeve 20 and the tube 10 in the region 24.

Because of the nature of the materials involved and geometry of the braze of the tube/sleeve sealed area, eddy-current testing is incapable of detecting lack of bonding voids in the braze which might result in leakage paths. The present invention makes it possible to identify such lack of bonding by ultrasonic testing.

The ultrasonic testing system which has been provided in accordance with the presently preferred embodiment of the invention includes a probe 26. The probe is a cylindrical member having a flat 28 along a diameter and a step 30. Ultrasonic transducers 32 and 34 (piezoelectric crystals) are embedded in the probe and project beams of ultrasonic energy towards the interior surface of the tube 20. The probe is shown positioned in the area of the seal 22 for the testing thereof. The probe is part of a rotational and axial drive scanner mechanism which delivers the ultrasonic energy to the seal area 22, rotates and axially indexes along the area 22 to scan the area and to provide signals from which a display of the interior of the region is produced. The ultrasonic energy, because of the close spacing and high resolution of the display which is desired, is preferably of a very high frequency (short wave length). A frequency of 20 MHz is used in accordance with this preferred embodiment of the invention. Higher frequencies may be used if greater resolution is needed.

The scanner has a support for the probe 26. This support is a wand 36. The wand 36 is a threaded tube, which provides a worm gear. The threads may be ground into the outer periphery of the tube as shown at 38. An axial drive mechanism for the tube is provided by a roller nut assembly 40 in which a roller nut 42 is fixed. The roller nut 42 is backed by pressure rollers which may be 120 degrees apart and disposed opposite to the roller nut 42. One of these pressure rollers 44 appears in the drawing. The roller nut assembly 40 is driven by a stepper motor 46 which is called the X motor. The X-motor is coupled to the assembly by gearing, illustrated as gears 48 and 50.

A reference tube 52 is disposed around the wand 36 together with a lamp assembly 54 including a circular flourescent lamp 56 within a transparent cover 58. A circular member 60 having a trough 62 which catches excess water used to couple the ultrasonic energy to the surface of the sleeve 20, is also disposed around the wand 36. A drain tube 64 carries the water from the trough 62 to a drain 66 which may be remote from the system and is shown nearby only to simplify the illustration. The reference tube 52, lamp assembly 54 and drain 60 are connected to a carriage indicated schematically as the block 68.

The roller nut assembly 40 together with the X-motor 46 and the gearing 48 and 50 and also together with the wand 36 and the probe 26 at the upper end thereof are rotated by another motor 70, called the Y-motor, through gearing illustrated as gears 72 and 74. The Y-motor is fixedly connected to the carriage 68.

The interior 76 of the tubular wand 36 provides a conduit for electrical leads from the transducers 32 and 34 and also for supply and drain pipes 78 and 80. These pipes are connected to L fittings 82 and 84 just below the probe 26 and above a seal 88. The seal defines a volume embracing the probe and covering the region 22 which is filled with liquid, suitably demineralized water 90. The water is supplied through the supply pipe 78 from a supply water tank 94 by a supply pump 96. After testing is completed, the water, which may be contaminated, because it is in the environment of the steam generator through which primary water from the reactor has passed, is drained through the drain pipe 80 by a return pump 98 into a reservoir 100.

A guide bar 102 which is attached to the carriage 68 supports the portion of the wand below the drive nut assembly 40. A coupling 104 connects the lower end of the wand 36 to a conduit 106, suitably armored cable, which contains the leads from the transducers 32 and 36 as well as the water tubes 78 and 80.

Supported on the guide bar 102 is an upper limit switch 110, called the XUL. A lower limit switch 112, called XLL is also attached to the guide bar 102. Attached to the carriage 68, and coupled to the roller nut assembly 40, is a limit switch which detects rotation in a clockwise direction 370 degrees and in a counter-clockwise direction also 370 degrees to indicate that there has been a complete rotational or circumferential scan (with a 10 degree overlap). This limit switch 114 is labeled YLSW.

The carriage 68 is connected to a manipulator 116 which is operated by a programmed computer controller 118. When the manipulator is in operation, the wand and the probe are retracted so that the probe is within the confines of the reference tube 52 and the entire assembly is below the lower ends of the tubes 10, 11 and 12. The manipulator pivots the carriage from center point within the lower channel head of the steam generator. The manipulator is an R-$\theta$ which may be designed in accordance with conventional robotic techniques. It moves the carriage and the probe radially (R) with respect to the center point of the steam generator and rotationally ($\theta$) into approximate alignment with the sleeved tube (in the exemplary case this will be sleeved tube 10/20). The manipulator may be operated manually in a fine control mode under observation of TV cameras 120; two of which, 90 degrees apart may be used. The TV cameras produce displays on TV screens 122. The light to illuminate the scene is provided by the lamp assembly 54. The probe and the scanner are then brought into alignment with the sleeve 20, with the reference tube spaced, a desired distance, for example $\frac{1}{4}$ of an inch, from the bottom of the tube and sleeve 10/20.

A computer controller 124 then commences a programmed sequence. Digital signals are provided through a translator controller 126, suitably a microprocessor programmed to develop a sequence of digital signals. The computer controller provides its digital signals to translators 128 and 130 which are referred to as the X translator and the Y translator. These tranlators are converter circuits which translate the digital signals into N successive pulses, where N is the number of steps through which the motor is to be driven. N in this first sequence of steps is sufficient to rotate the roller nut assembly so as to drive the probe 26 of the scanner where the beam of ultrasonic energy from the upper transducer 32 will project to the upper edge of the region 22 to be inspected. The lower transducer 34 is spaced from the upper transducer 28 an axial distance less than one-half of the length of the region 22. Two beams of ultrasonic energy are used so that the region may be scanned more quickly than would be the case if one beam alone were used. The overlap assures that there will be a complete axial scan of the area.

The computer controller then commands the translator controller 126 to provide signals to the Y translator 130 so as to produce a sequence of pulses to the Y motor 70 sufficient to cover a 370 degree scan circumferentially around the region. After a circumferential scan in one direction, the computer controller 124 provides a signal through the translator controller 126 to the X-translator 128 to index the probe downwardly, suitably approximately 0.032 of an inch. Then the circumferential scan, now in the opposite direction, is repeated. The procedure, axial indexing and rotation continues until the entire area of the region is covered. Inasmuch as two transducers, 32 and 34, are used only half the number of scans which would be required than if a single transducer were used is necessary. The limit switches 110, 112 and 114 provide inputs to the computer controller 124 to verify that the scanner has been driven axially and rotationally over the required distances.

An ultrasonic flaw detector signal generator and display device 131 is used to generate the ultrasonic signals and to respond to the reflected ultrasonic signals. The device 131 may be a commercial device which is available from Krautkrammer-Branson, Inc. of Stratford, Conn. (USA). The transmitted signals TSU and TSL are in the form of bursts of pulses of the ultrasonic energy. After each burst, received signals RSU and RSL from the upper and lower transducers 32 and 34, which are passed through buffer amplifiers, are detected. Suitable range gates are used in the detector 130 so as to respond only to reflections from the interior of the tube and sleeve 10/20. The display 132 in the device 131 shows the analog signals which are received.

The device 131 digitizes the received signals to provide output digitized signals RSUP and RSLP from the upper and lower transducers. These signals are sampled to provide 64 successive groups of digital signals (64 successive 8 bit bytes, for example). The average value of the signals in each of the groups is provided by an averager 136. There are, therefore, 64 bytes each constituting an average of the reflected energy during each circumferential scan. The timing of these average signals, indicates the position of the reflection during the scan. These signals are processed in a display generator 138 which drives an XY display 140 which may be on the screen of a CRT (display terminal). The interface region 144 between the tube 10 and the sleeve 20 where brazing occurs is indicated. This region is shown by light shade in the display, except for three spots 146, 148 and 150 where bonding has occurred. The display indicates that the region must be reheated in order to remelt the gold brazing alloy to provide a leak free braze. After rebrazing another test may be run. The digital signals from the display generator may also be used to provide a real time three dimensional print (3-D) display which will show discontinuities and voids in the braze region. The sampling circuits 134, the averager 136 and the display generator 138 may be implemented by suitably programming the computer in the computer controller 124.

Figure 1A:
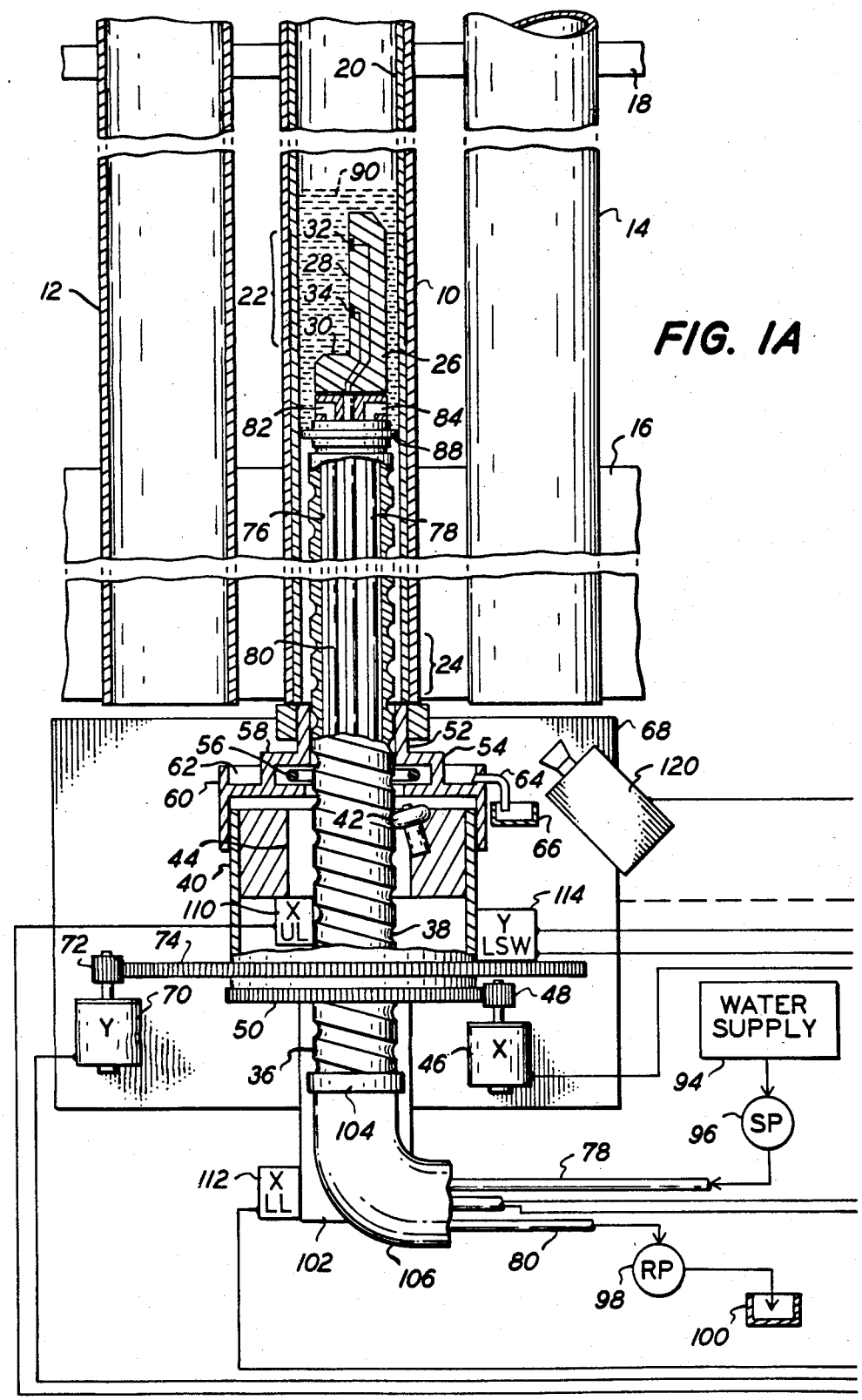
Figure 1B:
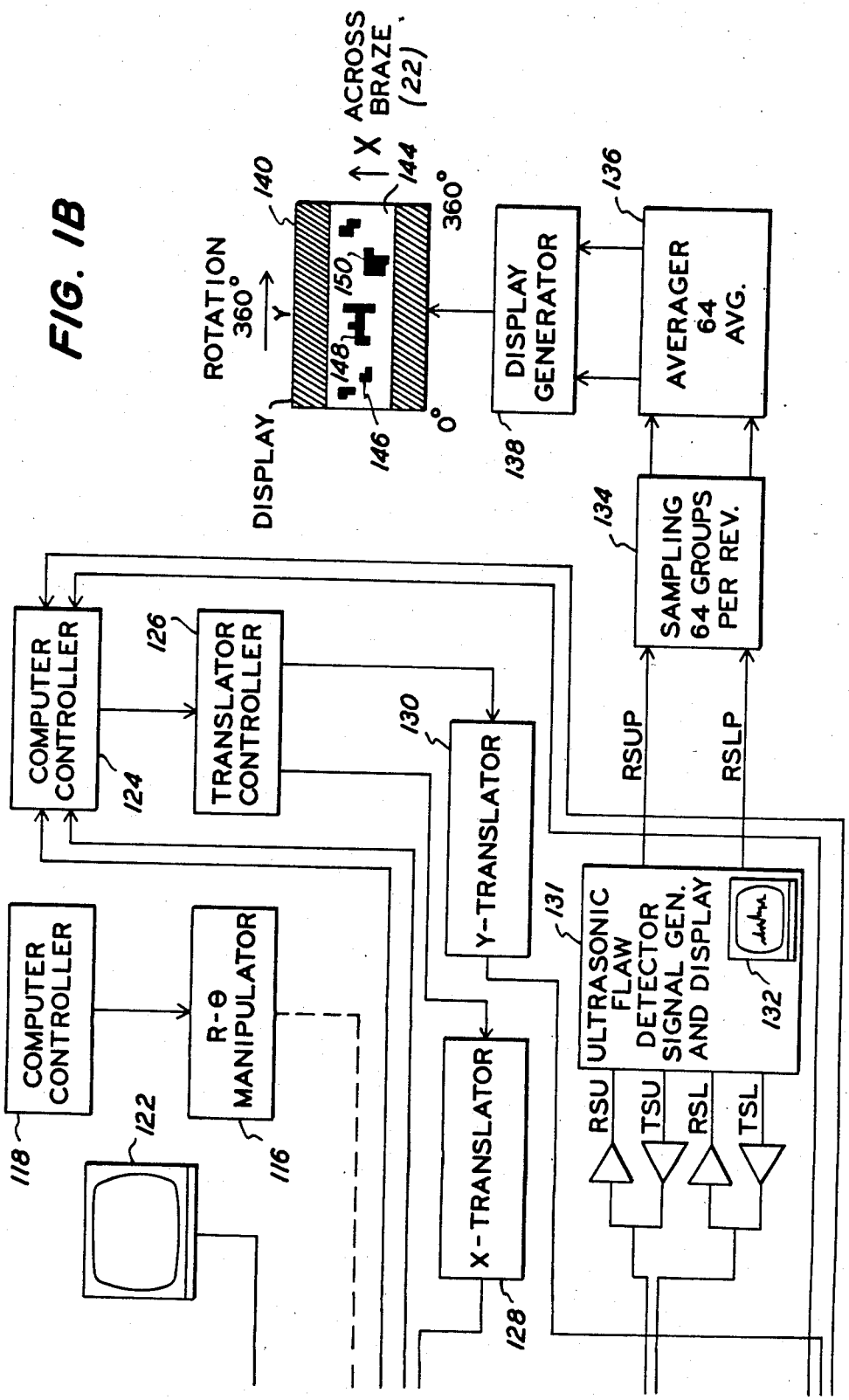

FIG. 3 shows the system installed in a steam generator of a nuclear plant. The electronic hardware of FIG. 1A is in two cabinets outside the containment area where the steam generator is located.

From the foregoing description, it will be apparent that there has been provided an improved ultrasonic inspection system for the inspection of tubular members and which is particularly adapted for the inspection of bonded areas between the sleeves and tubes in steam generators. Other applications for the invention as well as variations and modifications thereof, within the scope of the invention, will undoubtedly become apparent skilled in the art. Accordingly, the foregoing description should be taken as illustrative and not in a limiting sense.

What is claimed is:

1. A system for the inspection of tubular members which comprises means for transmitting ultrasonic signals in a direction from the interior towards the exterior of a tubular member having an internal cross-section and receiving reflections from any discontinuities in the material of said member, means for scanning an area of the interior of said tubular member extending axially and circumferentially thereof by directing said signals circumferentially around and axially along said tubular member, and means for processing said received signals to produce a display of said area of said member over which said signals are scanned which depicts any discontinuities in the internal cross-section of said member over said area.

2. The system according to claim 1 wherein said scanning means includes means for directing at least one beam of said signals at the interior of said member, and means for rotating said beam around the axis of said member at succesive positions spaced along said axis to cover said area.

3. The system according to claim 2 wherein said scanning means includes means for directing a plurality of beams spaced axially from each other to the interior surface of said tubular member to simultaneously scan a plurality of said ultrasonic signals.

4. The system according to claim 1 wherein said scanning means comprises at least one ultrasonic transducer, a probe containing said transducer, means for supporting said probe within the interior of said member, and rotational and axial drive means for moving said support means axially and rotating said support means for scanning said area of said tubular member.

5. The system according to claim 4 further comprising means providing a volume of fluid inside said tubular member around said probe for coupling said signals between the interior surface of said member and said transducer.

6. The system according to claim 4 wherein said supporting means is a wand member having a cross section smaller than the cross section of said tubular member, means for inserting said wand into said member, said drive means including means for rotating said wand and means for indexing said wand axially along said member between successive rotations thereof.

7. The system according to claim 6 wherein said wand is a tube having a worm thread on the outer periphery thereof, drive nut means rotatable around said tube comprising said indexing means, and said rotating means comprising means for rotating said tube together with said drive nut means around the axis of said tubular member.

8. The system according to claim 6 wherein said wand is a tube having a probe at the upper end thereof, seal means movable with said wand member and said probe engaging the interior surface of said tubular member and disposed below said probe transducer, conduits extending through said wand tube for supplying coupling liquid to and draining said liquid from the region inside said tubular member above said seal means which contains said probe, and electrical conductors connected to said transducer and also extending through said tube.

9. The system according to claim 6 further comprising a first stepper motor for operating said rotating means and a second stepper motor for operating said indexing means.

10. The system according to claim 9 wherein said rotating and indexing means further comprises means for detecting the completion of each rotation of said wand member, means for detecting when said wand member is at lower and upper limits of its axial travel, and means responsive to said detecting means for generating and applying separate pluralities of pulses to said first and second stepper motors to provide said successive rotational and indexing movements of said probe.

11. The system according to claim 10 wherein said pulse generating means comprises a programable data processor.

12. The system according to claim 1 wherein said processing means comprises means for detecting said signals reflected from said tubular member between the interior and exterior surfaces thereof, means for sampling said signals to provide outputs representing the presence and absence of voids at a plurality of successive locations spaced around the circumference of said tubular member during each circumferential scan thereof, and means responsive to said outputs for providing an X - Y display showing the location of any such voids where Y represents the circumferencial position of said scanning means and X represents the axial displacement of said scanning means.

13. The system according to claim 12 wherein said means for detecting said signals includes means for digitizing said detected signals, and a programable digital computer providing said sampling means and said X-Y display providing means.

14. The system according to claim 12 wherein said sampling means includes means for providing a plurality of successive groups of digital signals during each circumferential scan, and means for providing output digital signals corresponding to the average value of the signals in each group, said output digital signals being said outputs provided by said sampling means.

15. The invention as set forth in claim 14 wherein said X-Y display providing means is a display generator operated by said outputs and includes means for providing an image of said X-Y display.

16. The system according to claim 1 wherein a plurality of said tubular members are disposed axially aligned in a array, support means for supporting said ultrasonic signal transmitting and scanning means, and means for moving said support means perpendicularly to the axis of said tubular members in said array into alignment with selected ones of said tubular members so as to enable ultrasonic inspection of the selected ones of said members.

17. The system according to claim 16 wherein said moving means comprises R - $\theta$ manipulator means connected to said supported means.

18. The system according to claim 17 further comprising computer control means for operating said R - $\theta$ manipulator means for moving said supported means to bring said ultrasonic signal transmitting and scanning means into allignment with said selected ones of said tubular members at one end thereof.

19. The system according to claim 16 wherein said tubular members are steam generator tubes with sleeve inserts bonded thereto in said areas which are scanned by said ultrasonic signals.

* * * * *